US012433665B2

(12) United States Patent
Van Tol et al.

(10) Patent No.: US 12,433,665 B2
(45) Date of Patent: Oct. 7, 2025

(54) SURGICAL INSTRUMENTS INCORPORATING ULTRASONIC AND ELECTROSURGICAL FUNCTIONALITY

(71) Applicant: Covidien LP, Mansfield, MA (US)

(72) Inventors: David J. Van Tol, Boulder, CO (US); Thomas W. Meiser, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 155 days.

(21) Appl. No.: 18/087,035

(22) Filed: Dec. 22, 2022

(65) Prior Publication Data

US 2023/0124774 A1 Apr. 20, 2023

Related U.S. Application Data

(62) Division of application No. 16/238,812, filed on Jan. 3, 2019, now Pat. No. 11,564,733.

(Continued)

(51) Int. Cl.
*A61B 18/12* (2006.01)
*A61B 17/32* (2006.01)

(Continued)

(52) U.S. Cl.
CPC .. *A61B 18/1445* (2013.01); *A61B 17/320092* (2013.01); *A61B 18/1447* (2013.01);

(Continued)

(58) Field of Classification Search
CPC ............ A61B 18/1445; A61B 18/1447; A61B 2018/1452; A61B 2018/00994;

(Continued)

(56) References Cited

U.S. PATENT DOCUMENTS 617,247 A 1/1899 Gholson
1,352,978 A 9/1920 Lantieri (Continued)

FOREIGN PATENT DOCUMENTS

DE 202017004226 U1 10/2017
EP 2322111 A1 5/2011

(Continued)

OTHER PUBLICATIONS

Extended European Search Report issued in corresponding European Application No. 20201742.2 dated Feb. 10, 2021, 8 pages.

(Continued)

*Primary Examiner* — Daniel W Fowler

(57) ABSTRACT

A surgical instrument end effector assembly includes a first jaw member defining an insulative tissue-contacting surface and first and second electrically-conductive tissue-contacting surfaces disposed on either side of the insulative tissue-contacting surface. A second jaw member includes an ultrasonic blade body positioned to oppose the insulative tissue-contacting surface of the first jaw member. The first jaw member is movable relative to the second jaw member between a spaced-apart position and an approximated position to apply a first grasping force to tissue disposed therebetween. A slider is movable, independent of the first jaw member, between a retracted position, wherein the slider is disposed proximally of the first and second jaw members, and an extended position, wherein the slider extends about the first jaw member and urges the first jaw member from the approximated position further towards the second jaw member to apply a second, greater grasping force to tissue.

20 Claims, 3 Drawing Sheets

Related U.S. Application Data

(60) Provisional application No. 62/618,402, filed on Jan. 17, 2018, provisional application No. 62/618,241, filed on Jan. 17, 2018, provisional application No. 62/618,277, filed on Jan. 17, 2018, provisional application No. 62/618,292, filed on Jan. 17, 2018.

(51) Int. Cl.
*A61B 18/14* (2006.01)
*A61B 17/29* (2006.01)
*A61B 18/00* (2006.01)

(52) U.S. Cl.
CPC ................. *A61B 2017/2926* (2013.01); *A61B 2017/320075* (2017.08); *A61B 2017/320082* (2017.08); *A61B 2017/320094* (2017.08); *A61B 2017/320095* (2017.08); *A61B 2018/00196* (2013.01); *A61B 2018/00601* (2013.01); *A61B 2018/0063* (2013.01); *A61B 2018/00916* (2013.01); *A61B 2018/00922* (2013.01); *A61B 2018/00946* (2013.01); *A61B 2018/00994* (2013.01); *A61B 2018/1452* (2013.01)

(58) Field of Classification Search
CPC ........... A61B 2018/00946; A61B 2018/00916; A61B 2018/0063
See application file for complete search history.

(56) References Cited

U.S. PATENT DOCUMENTS

| | | | |
|---|---|---|---|
| 2,031,682 | A | 2/1936 | Wappler et al. |
| 3,685,518 | A | 8/1972 | Beuerle et al. |
| 3,911,241 | A | 10/1975 | Jarrard |
| 3,911,926 | A | 10/1975 | Peters |
| 4,003,380 | A | 1/1977 | Wien |
| 4,248,224 | A | 2/1981 | Jones |
| 4,478,219 | A | 10/1984 | Dujovny |
| 4,686,965 | A | 8/1987 | Bonnet |
| 4,712,545 | A | 12/1987 | Honkanen |
| 4,850,110 | A | 7/1989 | Meier, Jr. |
| 4,919,129 | A | 4/1990 | Weber, Jr. et al. |
| 5,190,517 | A | 3/1993 | Zieve et al. |
| 5,250,056 | A | 10/1993 | Hasson |
| 5,261,917 | A | 11/1993 | Hasson et al. |
| 5,261,918 | A | 11/1993 | Phillips et al. |
| 5,308,357 | A | 5/1994 | Lichtman |
| 5,312,329 | A | 5/1994 | Beaty et al. |
| 5,322,055 | A | 6/1994 | Davison et al. |
| 5,443,463 | A | 8/1995 | Stern et al. |
| 5,452,837 | A | 9/1995 | Williamson, IV et al. |
| 5,499,998 | A | 3/1996 | Meade |
| 5,810,811 | A | 9/1998 | Yates et al. |
| 6,152,923 | A | 11/2000 | Ryan |
| 6,251,110 | B1 | 6/2001 | Wampler |
| 6,257,241 | B1 | 7/2001 | Wampler |
| 6,416,486 | B1 | 7/2002 | Wampler |
| 6,562,032 | B1 | 5/2003 | Ellman et al. |
| 6,736,814 | B2 | 5/2004 | Manna et al. |
| 7,717,913 | B2 | 5/2010 | Novak et al. |
| 7,905,881 | B2 * | 3/2011 | Masuda ......... A61B 17/320092 606/51 |
| 8,221,417 | B2 | 7/2012 | Rioux et al. |
| 8,267,936 | B2 | 9/2012 | Hushka et al. |
| 8,529,565 | B2 | 9/2013 | Masuda |
| 8,764,747 | B2 | 7/2014 | Cummings et al. |
| 8,773,001 | B2 | 7/2014 | Wiener et al. |
| 9,700,366 | B2 | 7/2017 | Paulus |
| 11,446,079 | B2 | 9/2022 | Kabala et al. |
| 11,564,733 | B2 | 1/2023 | Van Tol et al. |
| 11,589,889 | B2 | 2/2023 | Meiser et al. |
| 2001/0051803 | A1 | 12/2001 | Desai et al. |
| 2002/0099373 | A1 | 7/2002 | Schulze et al. |
| 2002/0107517 | A1 | 8/2002 | Witt et al. |
| 2002/0165564 | A1 | 11/2002 | Danitz |
| 2003/0158549 | A1 | 8/2003 | Swanson |
| 2004/0068274 | A1 | 4/2004 | Hooven |
| 2006/0015095 | A1 | 1/2006 | Desinger et al. |
| 2006/0178667 | A1 | 8/2006 | Sartor et al. |
| 2007/0173814 | A1 | 7/2007 | Hixson et al. |
| 2007/0173872 | A1 | 7/2007 | Neuenfeldt |
| 2008/0172048 | A1 | 7/2008 | Martin et al. |
| 2008/0234710 | A1 | 9/2008 | Neurohr et al. |
| 2009/0125012 | A1 | 5/2009 | Rioux et al. |
| 2009/0248021 | A1 | 10/2009 | McKenna |
| 2010/0137854 | A1 | 6/2010 | Hosier |
| 2010/0145329 | A1 | 6/2010 | Bystryak et al. |
| 2010/0145335 | A1 | 6/2010 | Johnson et al. |
| 2010/0292716 | A1 | 11/2010 | Kasvikis et al. |
| 2011/0015627 | A1 | 1/2011 | DiNardo et al. |
| 2011/0087256 | A1 | 4/2011 | Wiener et al. |
| 2011/0238078 | A1 | 9/2011 | Goode |
| 2012/0150176 | A1 | 6/2012 | Weizman |
| 2012/0203143 | A1 | 8/2012 | Sanai et al. |
| 2013/0018364 | A1 * | 1/2013 | Chernov ............ A61B 18/1442 606/49 |
| 2013/0066311 | A1 | 3/2013 | Smith et al. |
| 2014/0005682 | A1 * | 1/2014 | Worrell ................. A61B 34/74 606/130 |
| 2014/0067015 | A1 | 3/2014 | Kothandaraman et al. |
| 2014/0114327 | A1 | 4/2014 | Boudreaux et al. |
| 2014/0135804 | A1 | 5/2014 | Weisenburgh, II et al. |
| 2014/0330271 | A1 | 11/2014 | Dietz |
| 2015/0088128 | A1 | 3/2015 | Couture |
| 2015/0141981 | A1 | 5/2015 | Price et al. |
| 2015/0148804 | A1 | 5/2015 | Rooks et al. |
| 2015/0148831 | A1 | 5/2015 | Faller et al. |
| 2015/0164531 | A1 | 6/2015 | Faller et al. |
| 2015/0164533 | A1 | 6/2015 | Felder et al. |
| 2015/0182251 | A1 | 7/2015 | Messerly et al. |
| 2015/0282867 | A1 | 10/2015 | Keller et al. |
| 2016/0015448 | A1 | 1/2016 | Longoria et al. |
| 2016/0038220 | A1 | 2/2016 | Twomey |
| 2016/0228138 | A1 | 8/2016 | Rodriguez-Navarro |
| 2016/0317216 | A1 | 11/2016 | Hermes et al. |
| 2017/0007317 | A1 | 1/2017 | Allen, IV et al. |
| 2017/0105754 | A1 | 4/2017 | Boudreaux et al. |
| 2017/0164973 | A1 | 6/2017 | Lesko |
| 2017/0164997 | A1 | 6/2017 | Johnson |
| 2017/0202570 | A1 | 7/2017 | Shelton, IV et al. |
| 2017/0202609 | A1 | 7/2017 | Shelton, IV |
| 2017/0333031 | A1 | 11/2017 | Al-Haqan |
| 2017/0354458 | A1 | 12/2017 | Wang |
| 2018/0125569 | A1 | 5/2018 | Vaders et al. |
| 2018/0368911 | A1 | 12/2018 | van Overdam |
| 2019/0216491 | A1 | 7/2019 | Meiser et al. |
| 2021/0038292 | A1 | 2/2021 | Kabala et al. |
| 2022/0387097 | A1 | 12/2022 | Kabala et al. |
| 2023/0200838 | A1 | 6/2023 | Meiser et al. |
| 2025/0009379 | A1 | 1/2025 | Meiser et al. |

FOREIGN PATENT DOCUMENTS

| | | | |
|---|---|---|---|
| EP | 2474280 | A1 | 7/2012 |
| EP | 2583633 | A1 | 4/2013 |
| EP | 2829245 | A1 | 1/2015 |
| EP | 2946737 | A1 | 11/2015 |
| EP | 3117790 | A1 | 1/2017 |
| WO | 9517855 | A1 | 7/1995 |
| WO | 2017100423 | A2 | 6/2017 |
| WO | 2017123837 | A2 | 7/2017 |

OTHER PUBLICATIONS

Extended European Search Report issued in European Application No. 19152026.1 dated Jun. 28, 2019, 6 pages.
Extended European Search Report issued in European Application No. 19152133.5 dated Jun. 28, 2019, 6 pages.
European Search Report issued in corresponding European Application No. 19152028.7 dated Jul. 17, 2019, 11 pages.

(56) References Cited

OTHER PUBLICATIONS

Extended European Search Report issued in corresponding European Application No. 20195714.9 dated Dec. 21, 2020, 8 pages.
Extended European Search Report issued in corresponding European Application No. 19152030.3 dated Apr. 10, 2019, 8 pages.
Partial European Search Report issued in corresponding European Application No. 19152028.7 dated Apr. 12, 2019, 12 pages.
Communication Pursuant to Article 94(3) EPC issued in corresponding European Application No. 19152028.7 dated May 7, 2021, 5 pages.
Advisory Action received for U.S. Appl. No. 16/238,668, mailed on Mar. 11, 2022, 4 pages.
Final Office Action received for U.S. Appl. No. 16/238,754, mailed on Apr. 11, 2022, 14 pages.
Final Office Action received for U.S. Appl. No. 16/238,812, mailed on Apr. 1, 2022, 10 pages.
Final Office Action received for U.S. Appl. No. 17/078,204, mailed on Apr. 3, 2023, 8 pages.
Final Office Action received for U.S. Appl. No. 17/078,204, mailed on Jan. 23, 2024, 12 pages.
Final Office Action received for U.S. Appl. No. 17/890,397, mailed on Nov. 25, 2024, 9 pages.
Non-Final Office Action received for U.S. Appl. No. 16/238,600, mailed on Feb. 24, 2022, 18 pages.
Non-Final Office Action received for U.S. Appl. No. 16/238,668, mailed on Aug. 31, 2021, 8 pages.
Non-Final Office Action received for U.S. Appl. No. 16/238,812, mailed on Oct. 15, 2021, 14 pages.
Non-Final Office Action received for U.S. Appl. No. 17/078,204, mailed on Dec. 20, 2022, 7 pages.
Non-Final Office Action received for U.S. Appl. No. 17/078,204, mailed on Sep. 28, 2023, 10 pages.
Non-Final Office Action received for U.S. Appl. No. 17/890,397, mailed on Aug. 14, 2024, 8 pages.

* cited by examiner

SURGICAL INSTRUMENTS INCORPORATING ULTRASONIC AND ELECTROSURGICAL FUNCTIONALITY

CROSS REFERENCE TO RELATED APPLICATION

This application is a divisional of U.S. patent application Ser. No. 16/238,812, filed on Jan. 3, 2019, which claims the benefit of and priority to U.S. Provisional Patent Application Nos. 62/618,241, 62/618,277, 62/618,292, and 62/618,402, all of which were filed on Jan. 17, 2018. This application is also related to U.S. patent application Ser. Nos. 16/238,600, 16/238,668, and 16/238,754, all of which were filed on Jan. 3, 2019. The entire contents of each of the above applications are hereby incorporated herein by reference.

BACKGROUND

1. Technical Field

The present disclosure relates to energy-based surgical instruments and, more particularly, to surgical instruments having end effector assemblies incorporating ultrasonic and electrosurgical functionality to facilitate treating, e.g., sealing and/or dissecting tissue.

2. Discussion of Related Art

Ultrasonic surgical devices are used in many surgical procedures. An ultrasonic surgical device may include, for example, an ultrasonic blade and a clamp mechanism to enable clamping tissue against the blade. Ultrasonic energy transmitted to the blade causes the blade to vibrate at very high frequencies (e.g., 55,500 times per second), which allows for heating tissue to treat tissue clamped against or otherwise in contact with the blade.

Electrosurgical devices are also used in many surgical procedures. An electrosurgical device may include, for example, opposing jaw members operable to clamp tissue therebetween and conduct energy, e.g., RF energy, through clamped tissue to treat tissue.

Devices that combine ultrasonic and electrosurgical energy into a single multi-functional device are known, but may not leverage the strengths of both technologies effectively. In particular, existing devices may have end effectors that are not optimized for the combined use of ultrasonic and electrosurgical energy.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

Provided in accordance with aspects of the present disclosure is a surgical instrument including an end effector assembly having first and second jaw members and a slider. The first jaw member defining an insulative tissue-contacting surface and first and second electrically-conductive tissue-contacting surfaces disposed on either side of the insulative tissue-contacting surface. The first and second electrically-conductive tissue-contacting surfaces are adapted to connect to a source of electrosurgical energy. The second jaw member includes an ultrasonic blade body adapted to receive ultrasonic energy from an ultrasonic waveguide and is positioned to oppose the insulative tissue-contacting surface of the first jaw member. The first jaw member is movable relative to the second jaw member between a spaced-apart position and an approximated position to apply a first grasping force to tissue disposed between the first and second jaw members. The slider is movable, independent of the movement of the first jaw member, between a retracted position, wherein the slider is disposed proximally of the first and second jaw members, and an extended position, wherein the slider extends about the first jaw member and urges the first jaw member from the approximated position further towards the second jaw member to apply a second, greater grasping force to tissue disposed between the first and second jaw members.

In an aspect of the present disclosure, the ultrasonic blade body is adapted to connect to a source of electrosurgical energy.

In an aspect of the present disclosure, the first and second electrically-conductive tissue-contacting surfaces are electrically-isolated from one another and energizable to different potentials for conducting electrosurgical energy therebetween.

In another aspect of the present disclosure, the first and second electrically-conductive tissue-contacting surfaces are electrically-coupled to one another and configured to conduct energy from the first and second electrically-conductive tissue-contacting surfaces to the ultrasonic blade body.

In still another aspect of the present disclosure, the surgical instrument further includes a housing, a shaft extending distally from the housing, and an ultrasonic waveguide extending through the shaft. The end effector assembly is supported at a distal end portion of the shaft and the slider is slidably disposed about the shaft.

In yet another aspect of the present disclosure, a trigger is operably associated with the housing and coupled to the first jaw member. The trigger is selectively actuatable to move the first jaw member relative to the second jaw member between the spaced-apart position and the approximated position.

In still yet another aspect of the present disclosure, an actuator is operably associated with the housing and coupled to the slider, the actuator is selectively actuatable to move the slider between the retracted position and the extended position.

In another aspect of the present disclosure, an activation button is disposed on the housing. The activation button is selectively activatable to supply electrosurgical energy and/or ultrasonic energy to the end effector assembly.

In another aspect of the present disclosure, the slider is shaped complementary to an outer surface of the first jaw member.

In another aspect of the present disclosure, the first jaw member includes a jaw body and a jaw liner disposed thereon. The jaw liner defines the insulative tissue-contacting surface.

Another surgical instrument provided in accordance with aspects of the present disclosure includes an end effector assembly having first and second jaw members. The first jaw member includes first and second electrodes and a flexible joint interconnecting the first and second electrodes. The flexible joint defines an insulative tissue-contacting surface and the first and second electrodes defines first and second electrically-conductive tissue-contacting surfaces, respectively, disposed on either side of the insulative tissue-contacting surface. The first and second electrodes are adapted to connect to a source of electrosurgical energy. The second jaw member includes an ultrasonic blade body adapted to receive ultrasonic energy from an ultrasonic waveguide and positioned to oppose the insulative tissue-contacting surface of the first jaw member. The first jaw member is movable relative to the second jaw member between a spaced-apart position and an approximated position. Upon movement of the first jaw member from the spaced-apart position to the approximated position, the flexible joint is flexed from a first configuration, wherein the insulative tissue-contacting surface and the first and second electrically-conductive tissue-contacting surfaces are generally co-planar, to a second configuration, wherein the first and second electrically-conductive tissue-contacting surfaces are angled inwardly towards one another.

In an aspect of the present disclosure, the first jaw member further includes first and second spaced-apart support shafts positioned adjacent the first and second electrodes, respectively. The first and second support shafts are movable relative to the second jaw member to move the first jaw member between the spaced-apart and approximated positions and to flex the flexible joint between the first configuration and the second configuration.

In another aspect of the present disclosure, in the approximated position of the first jaw member and the second configuration of the flexible joint, the first jaw member generally conforms about the second jaw member.

In yet another aspect of the present disclosure, the ultrasonic blade body is adapted to connect to a source of electrosurgical energy.

In still another aspect of the present disclosure, the first and second electrically-conductive tissue-contacting surfaces are electrically-isolated from one another and energizable to different potentials for conducting electrosurgical energy therebetween.

In still yet another aspect of the present disclosure, the first and second electrically-conductive tissue-contacting surfaces are electrically-coupled to one another and configured to conduct energy from the first and second electrically-conductive tissue-contacting surfaces to the ultrasonic blade body.

In another aspect of the present disclosure, the surgical instrument further includes a housing, a shaft extending distally from the housing, and an ultrasonic waveguide extending through the shaft. The end effector assembly is supported at a distal end portion of the shaft.

In yet another aspect of the present disclosure, a trigger is operably associated with the housing and coupled to the first jaw member. The trigger is selectively actuatable to move the first jaw member relative to the second jaw member between the spaced-apart position and the approximated position and to flex the flexible joint between the first configuration and the second configuration.

In another aspect of the present disclosure, an activation button is disposed on the housing. The activation button is selectively activatable to supply electrosurgical energy and/or ultrasonic energy to the end effector assembly.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 1:
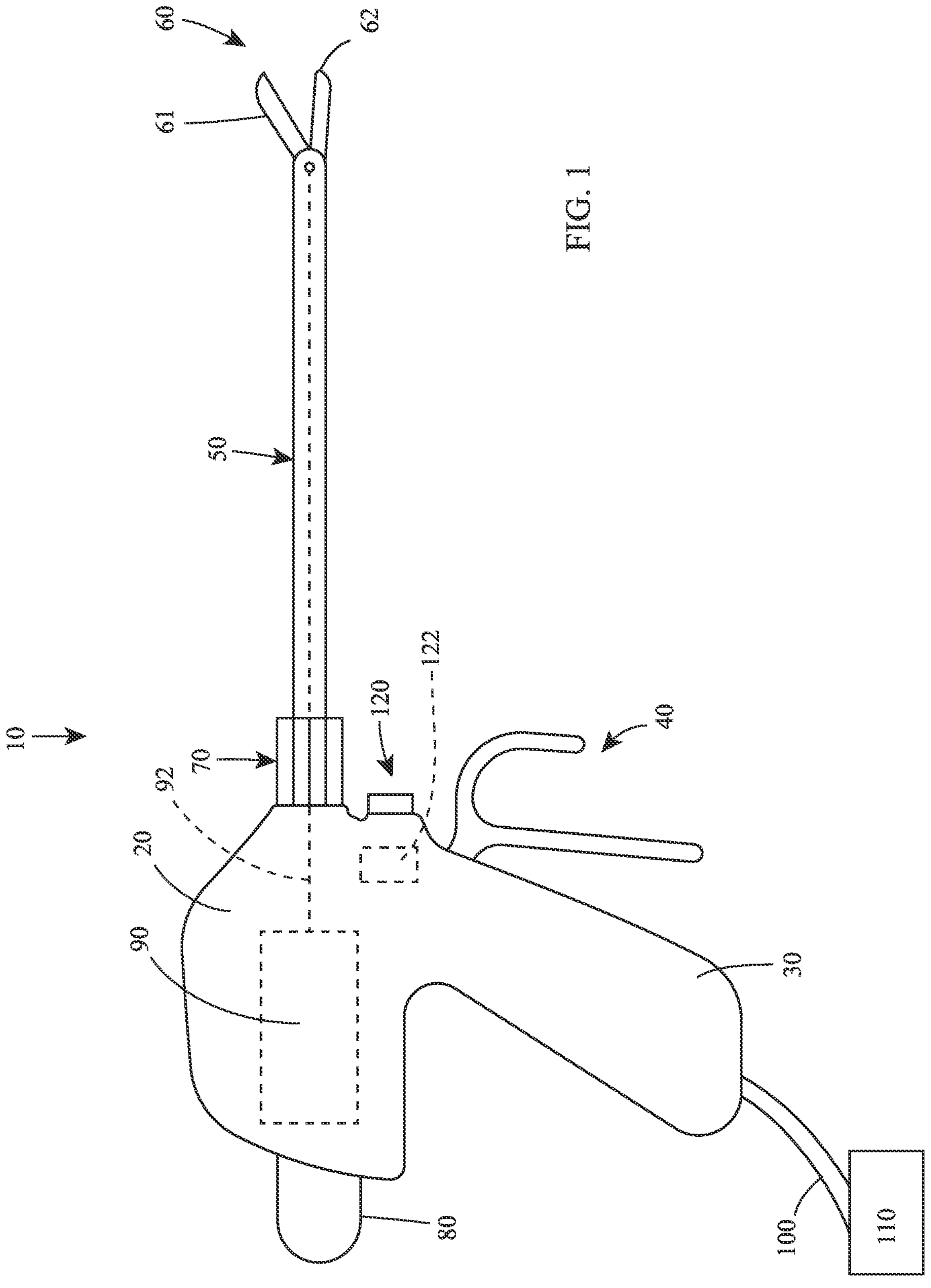
FIG. 1 is a side view of a surgical instrument exemplifying the aspects and features of the present disclosure.
Figure 2A:
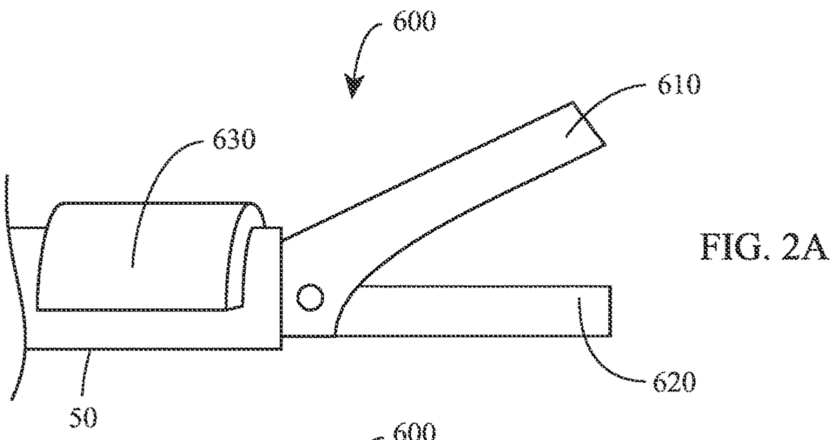
FIG. 2A is a side view of an end effector assembly configured for use with the surgical instrument of FIG. 1, wherein a first jaw member is spaced apart relative to a second jaw member and a slidable tube is disposed in a retracted position.
Figure 2B:
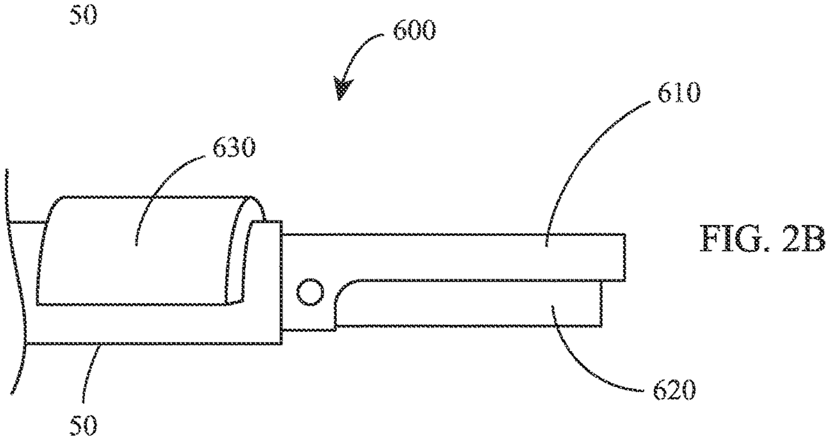
FIG. 2B is a side view of the end effector assembly of FIG. 2A, wherein the first jaw member is in an approximated position relative to the second jaw member and the slidable tube is maintained in the retracted position.
Figure 2C:
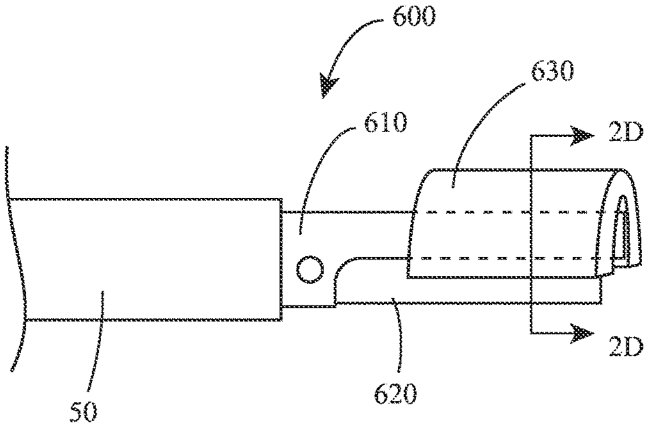
FIG. 2C is a side view of the end effector assembly of FIG. 2A, wherein the first jaw member is in an approximated position relative to the second jaw member and the slidable tube is disposed in an extended position.
Figure 2D:
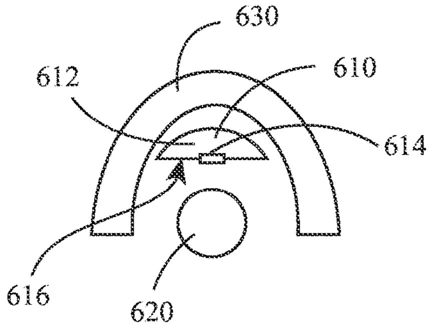
FIG. 2D is a transverse, cross-sectional view of the end effector assembly of FIG. 2A, taken across section line "2D-2D" in FIG. 2C.

Referring generally to FIG. 1, a combined electrosurgical, e.g., RF, and ultrasonic surgical instrument exemplifying the aspects and features of the present disclosure is shown and generally identified by reference numeral 10. For the purposes herein, surgical instrument 10 is generally described. Aspects and features of surgical instrument 10 not germane to the understanding of the present disclosure are omitted to avoid obscuring the aspects and features of the present disclosure in unnecessary detail.

Surgical instrument 10 generally includes a housing 20, a handle 30, a trigger 40, an elongated shaft 50, an end effector assembly 60, a rotating assembly 70, an actuator 80, an ultrasonic transducer 90, a cable 100 coupled to a surgical generator 110, and an activation switch 120. Activation switch 120 selectively activates a supply of electrosurgical energy from generator 110 to end effector 60 for treating tissue in an electrosurgical energy mode and selectively activates a supply of ultrasonic energy from ultrasonic transducer 90 (powered by generator 110) to end effector assembly 60 for treating tissue in an ultrasonic energy mode. To accomplish this, a switch box 122 disposed within housing 20 and coupled to actuator 80, activation switch 120, and/or generator 110 may be provided to determine the mode of surgical instrument 10 and enable the supply of the appropriate energy depending upon the mode. Alternatively, separate switches may be provided for each mode. Further, as an alternative to a separate generator 110, a generator and battery may be incorporated on or within housing 20 such that surgical instrument 10 operates as a cordless device.

With continued reference to FIG. 1, elongated shaft 50 of surgical instrument 10 extends distally from housing 20 and supports end effector assembly 60 at a distal end portion of elongated shaft 50. End effector assembly 60 is disposed at the distal end portion of elongated shaft 50 and includes first and second jaw members 61, 62, respectively, that cooperate to clamp and treat tissue, as described in further detail below. Rotating assembly 70 enables the selective rotation of elongated shaft 50 and, thus, end effector assembly 60 relative to housing 20. Actuator 80 is selectively manipulatable in any suitable fashion, e.g., rotated, pivoted, translated, combinations thereof, etc. to transition end effector assembly 60 between an ultrasonic configuration for use in the ultrasonic energy mode and an electrosurgical configuration for use in the electrosurgical energy mode. In embodiments where end effector assembly 60 need not be physically transitioned between the ultrasonic and electrosurgical energy modes, actuator 80 may be omitted.

Handle 30 is integrally associated with housing 20 for clamping and/or handling surgical instrument 10. Trigger 40 is movable relative to handle 30 from an initial position to an actuated position. Trigger 40 is operably coupled to a drive assembly (not shown) that mechanically imparts movement to end effector assembly 60. More specifically, actuation of trigger 40 causes first jaw member 61 to pivot relative to second jaw member 62 from a spaced-apart position to an approximated position to clamp tissue therebetween.

End effector assembly 60, as noted above, includes first and second jaw members 61, 62. Generally, in an ultrasonic mode, when activation switch 120 is activated, second jaw member 62 serves as an ultrasonic blade that is acoustically coupled to ultrasonic transducer 90 via a waveguide 92 to enable transmission of ultrasonic energy from ultrasonic transducer 90, along waveguide 92, to second jaw member 62 for treating tissue. In an electrosurgical mode, when activation switch 120 is activated, electrodes on one or both of the jaw members 61, 62 are energized to enable the conduction of electrosurgical energy through tissue clamped between jaw members 61, 62 to treat tissue. Various embodiments of end effector configurations suitable for use with surgical instrument 10 for the above purposes are described in detail below with reference to FIGS. 2A-3D. To the extent consistent, any of the aspects and features of the embodiments detailed below may be incorporated into any of the other embodiments.

Referring now to FIGS. 2A-2D, in conjunction with FIG. 1, in accordance with an embodiment of the present disclosure, an end effector assembly 600 is provided including first and second jaw members 610, 620, and a semi-tube slider 630 defining a substantially U-shaped cross-sectional profile. Semi-tube slider 630 is slidably disposed on a distal end portion of shaft 50 and operably coupled to actuator 80 via, for example, a drive member and/or other suitable structure (not shown) such that actuation of actuator 80, e.g., translation of actuator 80 relative to housing 20, slides semi-tube slider 630 between a retracted position (FIGS. 2A and 2B), wherein semi-tube slider 630 is proximal of jaw members 610, 620, and an extended position (FIGS. 2C and 2D), wherein semi-tube slider 630 is disposed about jaw members 610, 620. As can be appreciated, semi-tube slider 630 is only moved to the extended position when jaw members 610, 620 are disposed in the approximated position. Further, semi-tube slide 630 may be configured complementary to the outer surface of jaw member 610 to facilitate sliding thereabout.

Jaw members 610, 620 are configured for ultrasonic and electrosurgical energy delivery to tissue to treat tissue. More specifically, jaw member 610 includes a jaw body 612 defining a tissue-contacting surface 616, and a jaw liner 614. Tissue-contacting surface 616 of jaw body 612 is at least partially formed from or includes electrically-conductive material disposed thereon that is electrically coupled to generator 110 and activation switch 120, e.g., via one or more lead wires (not shown) extending through cable 100, housing 20, and elongated shaft 50. Jaw liner 614 may be formed from an insulative, compliant material, e.g., polytetraflouroethylene (PTFE), to reduce friction and facilitate clamping of tissue between jaw liner 614 and jaw member 620. Tissue-contacting surface 616 extends on either side of jaw liner 614 and may be energizable to a single potential, or may have multiple electrically-isolated portions (e.g., a first portion on one side of jaw liner 614 and a second portion on the other side of jaw liner 614) capable of being energized to different potentials.

Jaw member 620 is configured as an ultrasonic blade body configured to receive ultrasonic energy from waveguide 92 for treating tissue clamped between jaw member 620 and jaw liner 614 of jaw member 610. Jaw member 620 is also electrically coupled to generator 110 and activation switch 120, e.g., via one or more lead wires (not shown) extending through cable 100, housing 20, and elongated shaft 50, to enable energization thereof at a different potential relative to jaw member 610 to permit the conduction of electrosurgical energy to treat tissue clamped therebetween. Alternatively, jaw member 620 may remain electrically neutral, such that electrosurgical energy is conducted transversely relative to jaw members 610, 620 from one portion of tissue-contacting surface 616 to another portion thereof.

Depending upon the desired tissue treatment, end effector assembly 600 may operate in an ultrasonic mode, wherein jaw member 620 is supplied with ultrasonic energy to treat tissue clamped between jaw member 620 and jaw liner 614, while jaw member 610 remains unenergized. End effector assembly 600 may alternatively be operated in an electrosurgical energy mode, wherein jaw member 610 is supplied with electrosurgical energy at a first potential and jaw member 620 is supplied with electrosurgical energy as a second, different potential such that electrosurgical energy is conducted therebetween and through tissue to treat tissue. Further still, a combined mode may be provided wherein the ultrasonic and electrosurgical modes are operated simultaneously, in staggered but overlapping relation, or consecutively. When the electrosurgical or combined mode is desired, semi-tube slider 630 is advanced from the retracted position to the extended position to urge jaw member 610 further towards jaw member 620, thus increasing the jaw force applied to tissue to facilitate electrosurgical tissue treatment.

Figure 3B:
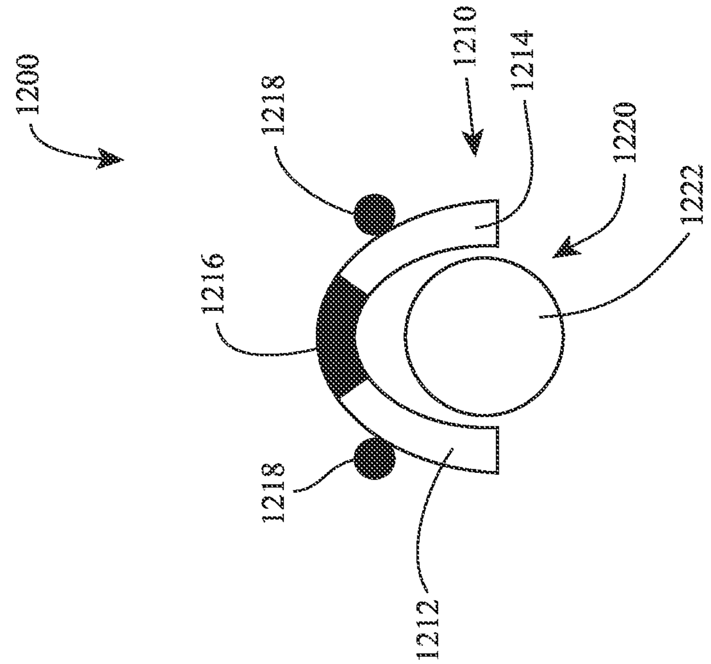
FIG. 3B is transverse, cross-sectional view of the end effector assembly of FIG. 3A, wherein the first jaw member is in an approximated position relative to the second jaw member.
Figure 3A:
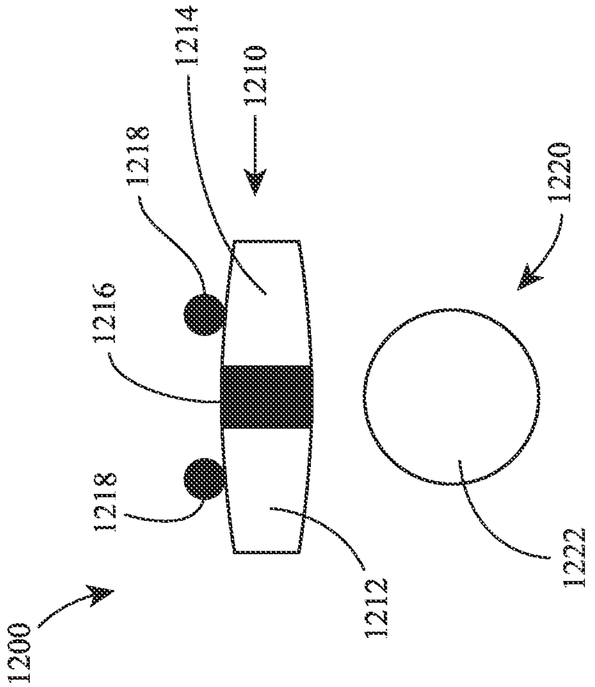
FIG. 3A is a transverse, cross-sectional view of yet another end effector assembly configured for use with the surgical instrument of FIG. 1, wherein a first jaw member view of the end effector assembly is spaced apart from a second jaw member thereof.

Referring now to FIGS. 3A and 3B, in conjunction with FIG. 1, another end effector assembly 1200 in accordance with the present disclosure is shown. End effector assembly 1200 generally includes first and second jaw members 1210, 1220. Jaw member 1210 includes a first electrode 1212, a second electrode 1214, a flex joint 1216 disposed therebetween, and a jaw frame including a pair of support shafts 1218 engaged to electrodes 1212, 1214. First and second electrodes 1212, 1214 are electrically coupled to generator 110 and activation switch 120, e.g., via one or more lead wires (not shown) extending through cable 100, housing 20, and elongated shaft 50, and may be energized to different potentials, for conducting electrosurgical energy transversely therebetween, or may be energized to the same potential for conducting electrosurgical energy between jaw members 1210, 1220.

Flex joint 1216 allows jaw member 1210 to transition from a substantially linear configuration (FIG. 3A), to a generally arcuate-shaped configuration (FIG. 3B), wherein electrodes 1212, 1214 are angled inwardly towards one another such that jaw member 1210 generally conforms about jaw member 1220. "Generally arcuate-shaped" and "generally conforms" are meant to account for the fact that electrodes 1212, 1214 remain linear, and just flex joint 1216 is transitioned to an arcuate configuration, although flexible electrodes are also contemplated. In the generally arcuate-shaped configuration (FIG. 3B), electrodes 1214 may be angled relative to ultrasonic blade body 1222 of second jaw member 1220 such as, for example, at an angle of 20 degrees to 70 degrees, in embodiments, at an angle of 30 degrees to 60 degrees, in embodiments, or, in still other embodiments, of about 45 degrees wherein (the "about" takes into account manufacturing, material, and other tolerances).

Support shafts 1218 are operably coupled to the drive assembly (not shown) extending between trigger 40 and end effector assembly 1200 such that, upon actuation of trigger 40, the drive assembly is actuated to pivot support shafts 1218 of first jaw member 1210 relative to second jaw member 1220 to thereby move first jaw members 1210 from the spaced-apart position to the approximated position relative to second jaw member 1220.

Flex joint 1216 may be formed of any suitable flexible material and/or components (springs, etc.) that enable flex joint 1216 to transition between the substantially linear configuration (FIG. 3A) and the arcuate-shaped configuration (FIG. 3B). Flex joint 1216 is biased towards the substantially linear configuration (FIG. 3A). Flex joint 1216 further acts as a jaw liner, and may be formed at least partially from and/or coated with a compliant, insulative material.

Second jaw member 1220 is an ultrasonic blade body 1222 that is acoustically coupled to waveguide 92 to enable transmission of ultrasonic energy from ultrasonic transducer 90, along waveguide 92, to ultrasonic blade body 1222. Ultrasonic blade body 1222 is also electrically coupled to generator 110 and activation switch 120, e.g., via one or more lead wires (not shown) extending through cable 100, housing 20, and elongated shaft 50, to enable ultrasonic blade body 1222 to be energized with electrosurgical energy.

In operation, upon actuation of trigger 40 to move jaw members 1210, 1220 towards the approximated position, as jaw member 1210 is initially moved towards jaw member 1220, jaw member 1210 is maintained in the substantially linear configuration (FIG. 3A). However, as jaw member 1210 is further moved towards jaw member 1220 such that flex joint 1216 contacts tissue disposed between jaw members 1210, 1220 and, thus, is inhibited from further movement towards jaw member 1220, the further movement of support shafts 1218 towards jaw member 1220 urges electrodes 1212, 1214 towards jaw member 1220, causing flex joint 1216 to flex from the substantially linear configuration (FIG. 3A) to the arcuate-shaped configuration (FIG. 3B) such that, upon reaching the approximated position, first jaw member 121 generally conforms about second jaw member 1220.

With jaw members 1210, 1220 in the approximated position clamping tissue therebetween, electrodes 1212, 1214 may be energized to different potentials, while ultrasonic blade body 1222 remains neutral, such that electrosurgical energy is conducted transversely through tissue to seal tissue clamped between jaw members 1210, 1220. Alternatively, electrodes 1212, 1214 may be energized to the same potential and ultrasonic blade body 1222 may be energized to a different potential such that electrosurgical energy is conducted therebetween to create two tissue seals, one on either side of ultrasonic blade body 1222. In either configuration, ultrasonic energy may be transmitted to ultrasonic blade body 1222 (simultaneously, overlapping, or consecutively with the supply of electrosurgical energy), to dissect the sealed tissue or tissue between the two tissue seals.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical instrument, comprising:

an end effector assembly, including:

a first jaw member including first and second electrodes and a flexible joint interconnecting the first and second electrodes, the flexible joint defining an insulative tissue-contacting surface and the first and second electrodes defining first and second electrically-conductive tissue-contacting surfaces, respectively, disposed on either side of the insulative tissue-contacting surface, the first and second electrodes adapted to connect to a source of electrosurgical energy; and a second jaw member including an ultrasonic blade body adapted to receive ultrasonic energy from an ultrasonic waveguide and positioned to oppose the insulative tissue-contacting surface of the first jaw member, wherein the first jaw member is movable relative to the second jaw member between a spaced-apart position and an approximated position, and wherein, upon movement of the first jaw member from the spaced-apart position to the approximated position, the flexible joint is flexed from a first configuration, wherein the insulative tissue-contacting surface and the first and second electrically-conductive tissue-contacting surfaces are generally co-planar, to a second configuration, wherein the first and second electrically-conductive tissue-contacting surfaces are angled inwardly towards one another.

2. The surgical instrument according to claim 1, wherein the first jaw member further includes first and second spaced-apart support shafts positioned adjacent the first and second electrodes, respectively, wherein the first and second support shafts are movable relative to the second jaw member to move the first jaw member between the spaced-apart and approximated positions and to flex the flexible joint between the first configuration and the second configuration.

3. The surgical instrument according to claim 1, wherein, in the approximated position of the first jaw member and the second configuration of the flexible joint, the first jaw member generally conforms about the second jaw member.

4. The surgical instrument according to claim 1, wherein the ultrasonic blade body is adapted to connect to a source of electrosurgical energy.

5. The surgical instrument according to claim 1, wherein the first and second electrically-conductive tissue-contacting surfaces are electrically-isolated from one another and energizable to different potentials for conducting electrosurgical energy therebetween.

6. The surgical instrument according to claim 1, wherein the first and second electrically-conductive tissue-contacting surfaces are electrically-coupled to one another and configured to conduct energy from the first and second electrically-conductive tissue-contacting surfaces to the ultrasonic blade body.

7. The surgical instrument according to claim 1, further comprising:

a housing;

a shaft extending distally from the housing; and an ultrasonic waveguide extending through the shaft, wherein the end effector assembly is supported at a distal end portion of the shaft.

8. The surgical instrument according to claim 7, further comprising a trigger operably associated with the housing and coupled to the first jaw member, the trigger selectively actuatable to move the first jaw member relative to the second jaw member between the spaced-apart position and the approximated position and to flex the flexible joint between the first configuration and the second configuration.

9. A surgical instrument, comprising:

an end effector assembly, including:

an ultrasonic blade body configured to transmit ultrasonic energy to tissue to treat tissue; and a jaw member including first and second tissue-contacting surfaces and a joint interconnecting the first and second tissue-contacting surfaces, the jaw member movable relative to the ultrasonic blade body between a spaced-apart position and an approximated position, wherein, upon movement of the jaw member from the spaced-apart position to the approximated position, the first and second tissue-contacting surfaces are rotated about an axis that is parallel to the ultrasonic blade body and moved relative to one another inwardly towards the ultrasonic blade body, and wherein the jaw member is configured to conduct electrosurgical energy through tissue to treat tissue.

10. The surgical instrument according to claim 9, wherein, in the approximated position, the jaw member generally conforms about the ultrasonic blade body.

11. The surgical instrument according to claim 9, wherein the jaw member and the ultrasonic blade body are configured to conduct electrosurgical energy therebetween and through tissue to treat tissue.

12. The surgical instrument according to claim 9, wherein the first and second tissue-contacting surfaces are electrically-conductive and electrically-isolated from one another by the joint.

13. The surgical instrument according to claim 12, wherein the first and second tissue-contacting surfaces are configured to conduct electrosurgical energy therebetween and through tissue to treat tissue.

14. The surgical instrument according to claim 9, wherein the joint is a flexible joint.

15. The surgical instrument according to claim 9, further comprising:

a housing;

a shaft extending distally from the housing, wherein the end effector is supported at a distal end portion of the shaft; and an ultrasonic transducer, the ultrasonic transducer configured to transmit ultrasonic energy to the ultrasonic blade body.

16. The surgical instrument according to claim 9, further comprising a first actuator operably coupled to the jaw member and configured to initiate movement of the jaw member between the spaced-apart position and the approximated position.

17. The surgical instrument according to claim 9, further comprising an activation switch configured, in a first mode, to at least initiate supply of ultrasonic energy to the ultrasonic blade body, and, in a second mode, to at least initiate supply of electrosurgical energy to the jaw member.

18. The surgical instrument according to claim 9, wherein, during a first portion of movement of the jaw member relative to the ultrasonic blade body from the spaced-apart position to the approximated position, the first and second tissue-contacting surfaces are maintained in an initial configuration and wherein, during a second portion of the movement of the jaw member relative to the ultrasonic blade body from the spaced-apart position to the approximated position, the first and second tissue-contacting surfaces are moved about the joint inwardly towards the ultrasonic blade body from the initial configuration to an angled configuration.

19. The surgical instrument according to claim 9, wherein the joint includes a compliant jaw liner configured to oppose the ultrasonic blade body in the approximated position.

20. A surgical instrument, comprising:

an end effector assembly, including:

an ultrasonic blade body configured to transmit ultrasonic energy to tissue to treat tissue; and a jaw member including first and second tissue-contacting surfaces and a joint interconnecting the first and second tissue-contacting surfaces, the jaw member movable relative to the ultrasonic blade body between a spaced-apart position and an approximated position, wherein, upon movement of the jaw member from the spaced-apart position to the approximated position, the first and second tissue-contacting surfaces are moved about the joint and relative to one another inwardly towards the ultrasonic blade body, and wherein the jaw member is configured to conduct electrosurgical energy through tissue to treat tissue, wherein the jaw member further includes first and second spaced-apart support shafts movable relative to the ultrasonic blade body to move the jaw member between the spaced-apart position and the approximated position and to move the first and second tissue-contacting surfaces about the joint.

* * * * *